(12) United States Patent
Hänsel et al.

(10) Patent No.: US 10,299,471 B2
(45) Date of Patent: May 28, 2019

(54) BIODEGRADABLE SUPER-SPREADING, ORGANOMODIFIED TRISILOXANE

(71) Applicant: Evonik Degussa GmbH, Essen (DE)

(72) Inventors: René Hänsel, Dorsten (DE); Ewald Sieverding, St. Johann (DE); Michael Ferenz, Essen (DE); Gerd Windbiel, Essen (DE); Andrea Jacobi, Essen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/574,513

(22) PCT Filed: May 30, 2016

(86) PCT No.: PCT/EP2016/062134
§ 371 (c)(1),
(2) Date: Nov. 16, 2017

(87) PCT Pub. No.: WO2016/202564
PCT Pub. Date: Dec. 22, 2016

(65) Prior Publication Data
US 2018/0125067 A1 May 10, 2018

(30) Foreign Application Priority Data
Jun. 16, 2015 (EP) .................... 15172382

(51) Int. Cl.
*A01N 25/30* (2006.01)
*C07F 7/08* (2006.01)
*A01N 25/06* (2006.01)
*C08G 65/336* (2006.01)

(52) U.S. Cl.
CPC ............. *A01N 25/30* (2013.01); *A01N 25/06* (2013.01); *C07F 7/0838* (2013.01); *C07F 7/0879* (2013.01); *C08G 65/336* (2013.01); *C08G 2230/00* (2013.01)

(58) Field of Classification Search
None
See application file for complete search history.

(56) References Cited

U.S. PATENT DOCUMENTS

| 6,734,141 B2 | 5/2004 | Humble et al. |
| 7,598,334 B2 | 10/2009 | Ferenz et al. |
| 7,605,284 B2 | 10/2009 | Brueckner et al. |
| 7,635,581 B2 | 12/2009 | Ferenz et al. |
| 7,727,599 B2 | 6/2010 | Doehler et al. |
| 7,776,989 B2 | 8/2010 | Ferenz et al. |
| 7,825,207 B2 | 11/2010 | Ferenz et al. |
| 7,834,122 B2 | 11/2010 | Ferenz et al. |
| 7,855,265 B2 | 12/2010 | Thum et al. |
| 7,893,128 B2 | 2/2011 | Busch et al. |
| 7,964,694 B2 | 6/2011 | Ferenz et al. |
| 8,030,366 B2 | 10/2011 | Ferenz et al. |
| 8,138,294 B2 | 3/2012 | Henning et al. |
| 8,158,572 B2 | 4/2012 | Schubert et al. |
| 8,163,673 B2 | 4/2012 | Giessler-Blank et al. |
| 8,172,936 B2 | 5/2012 | Herrwerth et al. |
| 8,198,473 B2 | 6/2012 | Ferenz et al. |
| 8,211,972 B2 | 7/2012 | Meyer et al. |
| 8,344,089 B2 | 1/2013 | Frey et al. |
| 8,362,095 B2 | 1/2013 | Schwab et al. |
| 8,420,748 B2 | 4/2013 | Henning et al. |
| 8,455,603 B2 | 6/2013 | Ferenz et al. |
| 8,466,248 B2 | 6/2013 | Meyer et al. |
| 8,486,677 B2 | 7/2013 | Thum et al. |
| 8,557,944 B2 | 10/2013 | Henning et al. |
| 8,580,225 B2 | 11/2013 | Haensel et al. |
| 8,617,529 B2 | 12/2013 | Herrwerth et al. |
| 8,685,376 B2 | 4/2014 | Czech et al. |
| 8,729,207 B2 | 5/2014 | Hartung et al. |
| 8,778,319 B2 | 7/2014 | Herrwerth et al. |
| 8,796,000 B2 | 8/2014 | Thum et al. |
| 8,802,744 B2 | 8/2014 | Knott et al. |
| 8,841,400 B2 | 9/2014 | Henning et al. |
| 8,883,932 B2 | 11/2014 | Brugger et al. |
| 8,916,511 B2 | 12/2014 | Maurer et al. |
| 8,946,369 B2 | 2/2015 | Henning et al. |
| 8,957,009 B2 | 2/2015 | Schubert et al. |
| 8,993,706 B2 | 3/2015 | Schubert et al. |
| 9,035,011 B2 | 5/2015 | Ferenz et al. |
| 9,175,126 B2 | 11/2015 | Albrecht et al. |
| 9,315,614 B2 | 4/2016 | Schubert et al. |
| 9,328,210 B2 | 5/2016 | Terheiden et al. |
| 9,334,354 B2 | 5/2016 | Ferenz et al. |
| 9,351,485 B2 | 5/2016 | Giessler-Blank et al. |
| 9,353,225 B2 | 5/2016 | Knott et al. |
| 9,441,145 B2 | 9/2016 | Schubert et al. |
| 9,539,549 B2 | 1/2017 | Haensel et al. |
| 9,550,928 B2 | 1/2017 | Lobert et al. |
| 9,657,144 B2 | 5/2017 | Hubel et al. |
| 9,706,771 B2 | 7/2017 | Poffenberger et al. |
| 9,790,327 B2 | 10/2017 | Klotzbach et al. |

(Continued)

FOREIGN PATENT DOCUMENTS

DE 10138382 A1 2/2003
DE 10148570 A1 4/2003
(Continued)

OTHER PUBLICATIONS

International Search Report—PCT/EP2016/062134—dated Jun. 27, 2016 (Year: 2016).*

(Continued)

*Primary Examiner* — Clinton A Brooks
*Assistant Examiner* — Kofi Adzamli
(74) *Attorney, Agent, or Firm* — Philip P. McCann; Nexsen Pruet PLLC

(57) ABSTRACT

The invention relates to polyether-modified siloxanes which are both superspreading and readily biodegradable. In particular, the invention is directed to a composition including polyether-modified siloxanes of formula (I)

$M_a D_b D'_c$    Formula (I)

with $M=R^1{}_3SiO_{1/2}$, $D=R^1{}_2SiO_{2/2}$, $D'=R^1R^2SiO_{2/2}$, where a is 2, b is between 0 and 0.1, c is between 1.0 and 1.15, 0 and 1.05, $R^1$ are independently hydrocarbyl having 1 to 8 carbon atoms, preferably methyl, ethyl, propyl or phenyl radicals, especially preferably methyl radicals, $R^2$ are independently a polyether radical of the formula (II)

$—R^3O[CH_2CH_2O]_m[CH_2CH(CH_3)O]_nR^5$    Formula (II)

where m=3.4 to 11.0, n=2.5 to 8.0, wherein m/n=1.9 to 2.8, and $R^3$ are independently divalent hydrocarbyl radicals having 2 to 8 carbon atoms, and $R^5$ is hydrogen, wherein the polyether-modified siloxanes of formula (I) having a biodegradability of greater than 60%.

20 Claims, No Drawings

(56) References Cited

U.S. PATENT DOCUMENTS

| | | |
|---|---|---|
| 2003/0118614 A1 | 6/2003 | Sieverding et al. |
| 2004/0014603 A1 | 1/2004 | Wollenweber et al. |
| 2005/0130842 A1 | 6/2005 | Fleute-Schlachter et al. |
| 2005/0244357 A1 | 11/2005 | Sieverding et al. |
| 2006/0155090 A1 | 7/2006 | Ferenz |
| 2006/0264330 A1 | 11/2006 | Zerrer et al. |
| 2007/0059539 A1 | 3/2007 | Doehler et al. |
| 2007/0197678 A1 | 8/2007 | Cavaleiro et al. |
| 2007/0213226 A1 | 9/2007 | Sieverding et al. |
| 2008/0187702 A1 | 8/2008 | Ferenz et al. |
| 2008/0269054 A1 | 10/2008 | Fleute-Schlachter et al. |
| 2009/0007483 A1 | 1/2009 | Hansel et al. |
| 2009/0029887 A1 | 1/2009 | Schwab et al. |
| 2009/0036334 A1 | 2/2009 | Schwab et al. |
| 2009/0053552 A1 | 2/2009 | De Gans et al. |
| 2009/0054238 A1 | 2/2009 | Fleute-Schlachter et al. |
| 2010/0029587 A1 | 2/2010 | Brueckner et al. |
| 2010/0034765 A1 | 2/2010 | Herrwerth et al. |
| 2010/0036011 A1 | 2/2010 | De Gans et al. |
| 2010/0210445 A1 | 8/2010 | Von Rymon et al. |
| 2010/0248325 A1 | 9/2010 | Eckstein et al. |
| 2011/0230619 A1 | 9/2011 | Kuppert et al. |
| 2013/0213267 A1 | 8/2013 | Fiedel et al. |
| 2013/0217930 A1 | 8/2013 | Haensel et al. |
| 2013/0259821 A1 | 10/2013 | Henning et al. |
| 2013/0267403 A1 | 10/2013 | Von Rymon et al. |
| 2013/0331592 A1 | 12/2013 | Hartung et al. |
| 2013/0345318 A1 | 12/2013 | Schubert et al. |
| 2014/0057819 A1 | 2/2014 | Haensel et al. |
| 2015/0329752 A1 | 11/2015 | Albrecht et al. |
| 2016/0075846 A1 | 3/2016 | Krebs et al. |
| 2016/0160009 A1 | 6/2016 | Ferenz et al. |
| 2016/0161001 A1 | 6/2016 | Jobe et al. |
| 2016/0249604 A1 | 9/2016 | Giessler-Blank et al. |
| 2016/0311963 A1 | 10/2016 | Lobert et al. |
| 2016/0319094 A1 | 11/2016 | Diendorf et al. |
| 2016/0340601 A1 | 11/2016 | Hänsel et al. |
| 2017/0065951 A1 | 3/2017 | Roland et al. |
| 2017/0094968 A1 | 4/2017 | Sieverding |
| 2017/0226285 A1 | 8/2017 | Lobert et al. |
| 2017/0283554 A1 | 10/2017 | Lobert et al. |
| 2017/0295782 A1 | 10/2017 | Klostermann et al. |

FOREIGN PATENT DOCUMENTS

| | | | |
|---|---|---|---|
| DE | 10314853 A1 | 10/2004 | |
| DE | 102004018926 A1 | 11/2005 | |
| DE | 102004034740 A1 | 2/2006 | |
| DE | 102005001040 A1 | 7/2006 | |
| DE | 102005006962 A1 | 8/2006 | |
| DE | 102006027776 A1 | 12/2007 | |
| DE | 102010001070 A1 | 7/2011 | |
| DE | 102010031094 A1 | 1/2012 | |
| EP | 1284212 A1 | 2/2003 | |
| EP | 1314356 A1 * | 5/2003 | ............ A01N 25/30 |
| EP | 1314356 A1 | 5/2003 | |
| EP | 1634940 A1 | 3/2006 | |
| EP | 1688453 A1 | 8/2006 | |
| EP | 1764394 A1 | 3/2007 | |
| EP | 1887024 A1 | 2/2008 | |
| EP | 1892327 A1 | 2/2008 | |
| EP | 2404950 A1 | 1/2012 | |
| EP | 3219738 A1 | 9/2017 | |
| WO | 1994022311 A1 | 10/1994 | |
| WO | WO-9422311 A1 * | 10/1994 | ............ A01N 25/30 |
| WO | 2002034051 A1 | 5/2002 | |
| WO | 03015512 A1 | 2/2003 | |
| WO | 2006081927 A1 | 8/2006 | |
| WO | 2013156237 A2 | 10/2013 | |
| WO | 2017133868 A1 | 8/2017 | |
| WO | 2017149069 A1 | 9/2017 | |

OTHER PUBLICATIONS

German language International Search Report dated Jun. 27, 2016 in PCT/EP2016/062134 (3 pages).

German language Written Opinion dated Jun. 27, 2016 in PCT/EP2016/062134 (5 pages).

International Search Report dated Jun. 27, 2016 in PCT/EP2016/062134 (2 pages).

Lobert et al., U.S. Appl. No. 15/540,605, filed Jun. 29, 2017.

Scheuermann et al., U.S. Appl. No. 15/546,297, filed Jul. 26, 2017.

* cited by examiner

BIODEGRADABLE SUPER-SPREADING, ORGANOMODIFIED TRISILOXANE

BACKGROUND

This application is a national stage application under 35 U.S.C. § 371 of International Application No. PCT/EP2016/062134 filed 30 May 2016, which claims priority to EP Application No. 15172382.2 filed 16 Jun. 2015, the disclosures of which are expressly incorporated herein by reference.

In crop protection, in pesticides and also in the industrial non-crop sector, the biological efficacy of such pesticides or pesticide mixtures is frequently improved by using what are called adjuvants or else auxiliaries or additives. Efficacy is frequently also referred to as effectiveness. The Pesticides Safety Directorate (PSD, the executive branch of the Health and Safety Executive (HSE), a non-governmental public organization in Great Britain) defines an adjuvant as a substance other than water which is not itself pesticidally active but increases the effectiveness of a pesticide. (http://www.pesticides.gov.uk/guidance/industries/pesticides/topics/pesticide-approvals/legislation/adjuvants-an-introduction). These are either added to the aqueous spray liquor shortly before deployment and spray application (as tankmix additive) or incorporated directly into crop protection composition formulations. With regard to the use of the word adjuvant, patents or the literature often use the terms surfactant or wetting agent synonymously, but these are much too wide-ranging and can therefore be interpreted as more of an umbrella term. Because of the use envisaged here, the term "adjuvant" is employed.

In practice, there are numerous crop protection active ingredients which achieve acceptable effectiveness, i.e. practically relevant efficacy, only with the aid of adjuvants. The adjuvants help here to compensate for the weaknesses of the active ingredient, for example the UV sensitivity of avermectins (destroyed by ultraviolet radiation) or the water instability of sulphonylureas. More recent active ingredients are generally water-insoluble and, in order therefore to be able to spread effectively over a target=target organism=plant, adjuvants are indispensable for the aqueous spray liquor, in order to compensate for the poor wetting of surfaces by way of a physical influence on the aqueous solutions. In addition, adjuvants help to overcome technical application problems, such as low water application rates, different water qualities and the trend to increased application rates. The increase in pesticide efficacy and the compensation for weaknesses in the crop protection compositions by adjuvants are generally referred to as increasing the activity or enhancing the effect of the crop protection composition application.

In crop protection, in pest control and in the industrial sector, chemical or biological crop protection compositions (also called pesticides hereinafter) or pesticide mixtures are employed. These may be, for example, herbicides, fungicides, insecticides, growth regulators, molluscicides, bactericides, virucides, micronutrients and biological crop protection compositions based on natural products or living or processed microorganisms. Active pesticidal ingredients are listed in connection with their fields of use, for example, in 'The Pesticide Manual', 14th edition, 2006, The British Crop Protection Council; biological active ingredients are specified in 'The Manual of Biocontrol Agents', 2001, The British Crop Protection Council. "Pesticide" is always used as a collective term hereinafter.

In order to be able to assess the agricultural potential and the activities of substances, it is necessary to carry out not only the laboratory and greenhouse experiments, but also realistic applications in agriculture, for example field trials.

In practice, crop protection compositions of this kind are often added to a tank with water as an ingredient and distributed in what is called the spray liquor with gentle stirring, in order to dilute the concentrated formulation of the active ingredient prior to spraying and to make it tolerable for the plants. Adjuvants are either incorporated into the crop protection formulation here prior to the tankmixing operation or added to the spray liquor as separate tankmix additives.

Adjuvants used are frequently synthetic surfactants, for example ethoxylated alcohols or alkyl polyglycosides. The use of water-soluble hydrophilic polyglyceryl esters as adjuvants in crop protection formulations is likewise known (WO 2002/034051, US 2006/0264330A1). In general, a feature common to these adjuvants is that they are water-soluble hydrophilic substances. Further adjuvants frequently used are additionally alkoxylated trisiloxane surfactants which lower the static surface tension of spray liquors or water to a greater degree than the organic surfactants used in the past, for example nonylphenol ethoxylates. Trisiloxane surfactants have the general structure Me3SiO—SiMeR—OSiMe3 where the R radical is a polyether radical. The use of superspreading trisiloxane surfactants, for example, BREAK-THRU® S-240, Evonik Industries AG, in combination with a pesticide, leads to an improvement in pesticide uptake by the plant and generally to a rise in the efficacy or effectiveness thereof. U.S. Pat. No. 6,734,141 states that this increase in effectiveness is occasioned specifically by a low surface tension and not necessarily by the spreading. The term "surface tension" is understood in the prior art to mean static surface tension. In the case of trisiloxanes, for example, static surface tension is about 20 to 25 mN/m.

WO1994022311 discloses superspreading compositions comprising polyether-modified siloxanes which may have two groups of polyethers: firstly polyethers having exclusively oxyethylene groups, and secondly polyethers which, in addition to oxyethylene groups, may also have oxypropylene groups. Experimental data are disclosed for modified siloxanes wherein the polyether residue contains exclusively oxyethylene groups. These are known, for example, as SILWET L-77.

A disadvantage of the prior art is that none of the superspreading trisiloxanes are biodegradable. For environmental reasons in particular, ever greater value is being placed on environmentally friendly products, particularly in order to gain popular acceptance with respect to chemical products in agriculture.

"Superspreading" in the context of the present invention is understood to mean that a 0.1 percent by weight solution in water, after examination in accordance with ASTM E2044-99 (2012), has a diameter of spread of at least 35 mm. Preferably, a droplet of a 0.1 percent by weight solution in water having a volume of 50 μm on a polypropylene film spreads to an area of at least 10 $cm^2$. Preferably, the spread is examined at 25° C.; preferably, the spread is determined at a relative air humidity of 60% and a pressure of 1013 mbar.

"Readily biodegradable" within the scope of the present invention describes degradability according to OECD Method 301F CD, preferably as described in the examples.

SUMMARY

It was an object of the present invention to overcome at least one disadvantage of the state of the art.

It has been found that, surprisingly, compositions comprising polyether-modified siloxanes as described in the claims are both superspreading and readily biodegradable.

The present invention provides compositions comprising polyether-modified siloxanes of formula (I)

$$M_a D_b D'_c \qquad \text{Formula (I)}$$

with $M=R^1_3SiO_{1/2}$, $D=R^1_2SiO_{2/2}$, $D'=R^1R^2SiO_{2/2}$,
where
a is 2
b is between 0 and 0.1, preferably 0,
c is between 1.0 and 1.15,
preferably between 1.0 and 1.10, especially preferably between 1.00 and 1.05,
$R^1$ are independently hydrocarbyl having 1 to 8 carbon atoms, preferably methyl, ethyl, propyl or phenyl radicals, especially preferably methyl radicals,
$R^2$ are independently a polyether radical of the formula (II)

$$-R^3O[CH_2CH_2O]_m[CH_2CH(CH_3)O]_nR^5 \qquad \text{Formula (II)}$$

where
m=3.4 to 11.0, preferably 3.6 to 9.9, more preferably 4.5 to 8.5,
n=2.5 to 8.0, preferably 2.7 to 7.5, more preferably 3.0 to 6.0,
but with the provisos that:
m/n=1.9 to 2.8,
$R^3$ are independently divalent hydrocarbyl radicals having 2 to 8 carbon atoms, preferably ethylene, propylene, 1-methylpropylene, 1,1-dimethylpropylene radical, especially preferably —$CH_2CH_2CH_2$—,
$R^5$ is hydrogen,
the polyether-modified siloxanes of formula (I) having a biodegradability of greater than 60%, more preferably of greater than or equal to 63% and especially preferably of greater than or equal to 65%, the maximum value being 100%.

Preferably, the polyether radical, calculated without $R^3O$ and calculated without $R^5$, has a molar mass M (PE) calculated by 44 g/mol*m+58 g/mol*n where the indices m and n relate to formula (II).

The preferred values of M (PE) are: lower limits M (PE) greater than 520 g/mol, preferably greater than 530 g/mol, more preferably greater than 535 g/mol; upper limit M (PE) less than 660 g/mol, preferably less than 630 g/mol, more preferably less than 600 g/mol.

Preferably, the value of M (PE) is greater than 520 g/mol and less than 660 g/mol, especially greater than 535 g/mol and less than 600 g/mol.

Preferably, the sum total of m+n is greater than 9 up to 19, more preferably greater than 9.5 up to 15 and especially preferably greater than 10 up to 12.

More preferably, the inventive compositions include the polyether-modified siloxanes of the formula (I) with an index c between 1 and 1.05, where the indices of the polyether radical of formula (II) are m from 3.4 to 11.0 and n from 2.5 to 8.0.

More preferably, the inventive compositions include the polyether-modified siloxanes of the formula (I) with an index c between 1 and 1.05, where the ratio m/n is 1.9 to 2.8.

Especially preferably, the inventive compositions include the polyether-modified siloxanes of the formula (I) with an index c between 1 and 1.05, where the molar mass of the polyether residue M(PE) is greater than 520 g/mol and less than 660 g/mol.

Especially preferably, the inventive compositions include the polyether-modified siloxanes of the formula (I) with an index c between 1 and 1.05, where the $R^5$ radical is hydrogen.

Especially preferably, the inventive compositions include the polyether-modified siloxanes of the formula (I) with an index c between 1 and 1.05, where the molar mass of the polyether residue M(PE) is greater than 520 g/mol and less than 660 g/mol and the $R^5$ radical is hydrogen.

Preferably, the inventive compositions do not include any further polyether-modified siloxanes apart from those of formula (I).

One advantage of the inventive compositions is that they have superspreading properties in water in the sense defined above. For this purpose, the area of a droplet on a polypropylene film is determined as described in detail in the examples.

Preferably, the inventive compositions have, as a 0.1 percent by weight solution in water, a spreading area of 10 to 60 $cm^2$, preferably of 15 to 50 $cm^2$ and more preferably of 20 to 40 $cm^2$. More preferably, the inventive compositions have the aforementioned spreads at a temperature of 25° C.

Polyether-modified siloxanes of formula (I) in which index c is at least 1.2 are known according to U.S. Pat. No. 6,734,141 as non-spreading compounds and are excluded from the present invention.

Preferably, the inventive compositions include the polyether-modified siloxanes of the formula (I) where the index d is 1.0 to 1.05 and a 0.1 percent by weight solution of these siloxanes in water has a spreading area of 15 to 60 $cm^2$.

More preferably, the inventive compositions include the polyether-modified siloxanes of the formula (I) having an index c between 1 and 1.05, where the m/n ratio is 0.8 to 2.8 and a 0.1% by weight solution of these siloxanes in water has a spreading area of 15 to 60 $cm^2$.

A further advantage of the inventive compositions is their biodegradability.

Biodegradability is preferably determined by the OECD 301 F method. More preferably, biodegradability is determined in accordance with OECD 301 F after 28 d at 22° C. Especially preferably, biodegradability is determined as described in the examples.

preferably, the polyether-modified siloxanes of formula (I) in the inventive compositions have a biodegradability of greater than 60%, more preferably of greater than or equal to 63% and especially preferably of greater than or equal to 65%, the maximum value being 100%.

Preferably, the inventive compositions include the polyether-modified siloxanes of the formula (I) where the index d is 1.0 to 1.05 and biodegradability of the siloxanes is greater than 60%.

More preferably, the inventive compositions include the polyether-modified siloxanes of the formula (I) having a biodegradability of greater than 60%, and the index c is additionally between 1 and 1.05, where the molar mass of the polyether radical M(PE) is greater than 520 g/mol and less than 660 g/mol and the $R^5$ radical is hydrogen.

More preferably, the inventive compositions include the polyether-modified siloxanes of the formula (I) having a biodegradability of greater than 60%, and the index c is additionally between 1 and 1.05, where the molar mass of the polyether radical M(PE) is greater than 520 g/mol and less than 660 g/mol, the $R^5$ radical is hydrogen and a 0.1% by weight solution of these siloxanes in water has a spreading area of 15 to 60 $cm^2$.

Preferably, the inventive compositions do not include any non-biodegradable polyether-modified siloxanes.

The present invention further provides a process for producing polyether-modified siloxanes, in which, in a first step, an H-siloxane of the formula (V)

$$M_a D_b D'_d \qquad (V)$$

with $M=R^1{}_3SiO_{1/2}$; $D=R^1{}_2SiO_{2/2}$, $D'=R^1R^2SiO_{2/2}$, where
a is 2,
b is between 0 and 0.1,
d is between 1.16 and 3,
$R^1$ are independently hydrocarbyl having 1 to 8 carbon atoms, preferably methyl, ethyl, propyl or phenyl radicals, especially preferably methyl radicals,
$R^2$ is hydrogen
is purified and, in a second step, is reacted in the manner of a hydrosilylation with a terminally unsaturated polyether of the formula (VI)

$$R^4O[CH_2CH_2O]_m[CH_2CH(CH_3)O]_nR^5 \qquad (VI)$$

where
m=3.4 to 11.0, preferably 3.6 to 9.9, more preferably 4.5 to 8.5,
n=2.5 to 8.0, preferably 2.7 to 7.5, more preferably 3.0 to 6.0,
but with the provisos that:
m/n=0.44 to 3.08, preferably 0.55 to 3.00, more preferably 0.8 to 2.8, especially preferably 1.9 to 2.8,
$R^5$ are each independently hydrocarbyl radicals having 1 to 16 carbon atoms or hydrogen, preferably hydrogen or methyl, especially hydrogen,
$R^4$ are independently monovalent terminally unsaturated hydrocarbyl having 2 to 8 carbon atoms, preferably $CH_2=CH_2-$, $CH_2=CHCH_2-$, $CH_2=CHCH(CH_3)-$, $CH_2=CHC(CH_3)_2$, especially preferably $CH_2=CHCH_2-$.

Preferably, the H-siloxane of formula (V) is purified in the first step of the process according to the invention by subjecting the H-siloxane to a suitable thermal separation process. Thermal separation processes are known by this term to those skilled in the art and include all processes based on the establishment of a thermodynamic phase equilibrium. Preferred thermal separation processes are selected from the list comprising distillation, rectification, adsorption, crystallization, extraction, absorption, drying and freezing-out, particular preference being given to methods of distillation and rectification. Particular preference is given to distillation and rectification under standard pressure.

Especially preferred is distillation and rectification at standard pressure for the compounds of the formula (V) with $R^2$=hydrogen and the indices a and b=zero and d=1.16 to 1.22 at a top temperature of 142° C. under standard pressure for purification of the product.

Preferably, in the process according to the invention, no H-siloxanes of the formula (V) which have been subjected to any separation process other than a thermal separation process are employed.

The index d of the compounds of the formula (V) can be determined by prior art methods, preferably with the aid of 1H NMR spectroscopy, more preferably by the method as described in the examples.

The hydrosilylation reaction in the process according to the invention is preferably catalysed with the aid of the platinum group catalysts familiar to those skilled in the art, more preferably with the aid of Karstedt catalysts.

The hydrosilylation reaction in the process according to the invention is preferably brought to a full conversion in relation to the hydrogen content of the H-siloxane of the formula (V). In the context of the present invention, full conversion is understood to mean that the conversion of SiH functions is >99%. This is detected in a manner familiar to those skilled in the art, preferably by gas-volumetric means after alkaline breakdown. This can be done, for example, by reacting a sample of the reaction mixture with a butanolic sodium butoxide solution (w (sodium butoxide)=5%) and concluding the amount of SiH functions still present from the amount of hydrogen formed.

The polyethers of the formula (VI) and the polyethers of the formula (II) may have a statistical construction. Statistical distributions are of blockwise construction with any desired number of blocks and with any desired sequence or are subject to a randomized distribution; they may also have an alternating construction or else form a gradient over the chain; more particularly they can also form any mixed forms in which groups with different distributions may optionally follow one another. Specific executions may result in restriction of the statistical distributions by virtue of the execution. For all ranges which are not affected by the restriction, there is no change in the statistical distribution.

Further preferably, it is also true of the polyethers of the formula (VI) in the process according to the invention that the polyether radical of formula (VI), calculated without $R^4O$ and calculated without $R^5$, has a molar mass M (PE) calculated by 44 g/mol*m+58 g/mol*n where the indices m and n are as defined for formula (II).

The preferred values for M (PE) are: lower limits for M (PE) greater than 520 g/mol, preferably greater than 530 g/mol, more preferably greater than 535 g/mol; upper limits for M (PE) less than 660 g/mol, preferably less than 630 g/mol, more preferably less than 600 g/mol.

Preferably, the value of M (PE) is greater than 520 g/mol and less than 660 g/mol, especially greater than 535 g/mol and less than 600 g/mol.

Preferably, the sum total of m+n is greater than 9 up to 19, more preferably greater than 9.5 up to 15 and especially preferably greater than 10 up to 12.

More preferably, $R^5$ is hydrogen and the value of M (PE) is greater than 520 g/mol and less than 660 g/mol; especially preferably, $R^5$ is hydrogen and the value of M (PE) is greater than 535 g/mol and less than 600 g/mol.

More preferably, the inventive H-siloxanes of the formula (V) have an index d between 1 and 1.05 and are reacted with terminally unsaturated polyethers of the formula (VI), where the indices m are from 3.4 to 11.0 and n from 2.5 to 8.0.

More preferably, the inventive H-siloxanes of the formula (V) have an index d between 1 and 1.05 and are reacted with terminally unsaturated polyethers of the formula (VI), where the m/n ratio is 0.8 to 2.8.

More preferably, the inventive H-siloxanes of the formula (V) have an index d between 1 and 1.05 and are reacted with terminally unsaturated polyethers of the formula (VI), where the m/n ratio is 1.9 to 2.8.

Especially preferably, the inventive H-siloxanes of the formula (V) have an index d between 1 and 1.05 and are reacted with terminally unsaturated polyethers of the formula (VI), where the molar mass of the polyether radical M(PE) is greater than 520 g/mol and less than 660 g/mol.

Especially preferably, the inventive H-siloxanes of the formula (V) have an index d between 1 and 1.05 and are reacted with terminally unsaturated polyethers of the formula (VI), where the $R^5$ radical is hydrogen.

Especially preferably, the inventive H-siloxanes of the formula (V) have an index d between 1 and 1.05 and are reacted with terminally unsaturated polyethers of the formula (VI), where the molar mass of the polyether radical M(PE) is greater than 520 g/mol and less than 660 g/mol and the $R^5$ radical is hydrogen.

Especially preferably, the inventive H-siloxanes of the formula (V) have an index d between 1 and 1.05 and are reacted with terminally unsaturated polyethers of the formula (VI), where the $R^5$ radical is hydrogen and where the m/n ratio is 1.9 to 2.8.

Preferably, the products of the process according to the invention do not include any further polyether-modified siloxanes that do not correspond to the products of the process according to the invention.

The inventive compositions can be produced by the prior art methods, but preferably by the process according to the invention.

The present invention further provides for the use of the inventive compositions and/or of the inventive process products as adjuvant in crop protection.

The inventive adjuvant is suitable with all crop protection compositions for all plants. Advantageously, the adjuvant is used together with herbicides, fungicides, insecticides, growth regulators and macro- and micronutrients (fertilizers), preferably with herbicides. The crop protection compositions and fertilizers may be either of synthetic origin or of biological and natural origin.

The inventive compositions may include further components. These further components may be selected from herbicides, fungicides, insecticides, growth regulators and fertilizers, preferably herbicides. Preferred fertilizers are macro- and micronutrients.

Preferably, the inventive compositions are used as a tankmix additive for spray liquors. Preferred use concentrations here are between 0.001% and 1% by volume, preferably between 0.01% and 0.5% by volume and more preferably between 0.02% and 0.15% by volume (also corresponding to about 0.1% by weight) of the spray liquor. This is equivalent to 10 to 3000 ml/ha when typically 100 to 1000 l of spray liquor per ha are deployed, and preferably an amount of adjuvant of 50 to 700 ml/ha, which are also added by the respective amounts of spray liquor irrespective of the total water application rate per ha.

Active substances are those which are approved and/or registered and/or listed in the individual countries for use on plants and crops in order to protect plants against damage, or to prevent yield loss as the result of pests or the like in a crop, or to eliminate undesirable accompanying flora, such as broad-leaved weeds and/or grass weeds, or to supply the plants with nutrients (also termed fertilizers). Active substances may be synthetic substances or else biological substances. Active substances may also be extracts, or natural substances, or antagonistically active organisms. They are usually also referred to as pesticides or plant protection agents. In general, active substances are incorporated into formulations for handling and efficiency purposes.

For use on plants or plant parts, crop protection composition formulations are usually diluted with water before the standard spraying through nozzles, and contain not only the active component but also other adjuvants such as emulsifiers, dispersing aids, antifrost agents, antifoams, biocides and surface-active substances such as surfactants. Active substances, especially fungicides, insecticides and nutrients, alone or in combination and having been provided with the other auxiliaries specified above, can also be applied to seeds (seed) of plants by various methods. Such methods are also referred to as seed treatment methods. The treatment of seed with fungicides and insecticides can protect plants in the early stage of growth from diseases and attack by insects.

The inventive compositions comprising the polyether-substituted siloxanes of the formula (I), the process according to the invention and the inventive use of the compositions and/or process products are described by way of example hereinafter, without any intention that the invention be restricted to these illustrative embodiments. If ranges, general formulae or compound classes are specified hereinafter, this shall encompass not only the corresponding ranges or groups of compounds that are explicitly mentioned, but also all sub-ranges and sub-groups of compounds which can be obtained by extracting individual values (ranges) or compounds. Where documents are cited in the context of the present description, it is intended that their content shall form a full part of the disclosure content of the present invention. Where percentages are given below, they are percentages in % by weight unless stated otherwise. In the case of compositions, the % figures, unless otherwise indicated, are based on the overall composition. Where average values are reported below, the averages in question are mass averages (weight averages), unless otherwise indicated. Where measurement values are reported above and below, these measurement values, unless stated otherwise, have been determined under a pressure of 101 325 Pa (standard pressure) and at a temperature at 25° C.

EXAMPLES

General Methods and Materials:

| Trade name | |
|---|---|
| Silwet L-77 | Product and trademark of Momentive |
| Silwet 806 | Product and trademark of Momentive |
| BREAK-THRU S 240 | Product and trademark of Evonik Degussa GmbH, Germany |
| BREAK-THRU S 278 | Product and trademark of Evonik Degussa GmbH, Germany |
| BREAK-THRU S 233 | Product and trademark of Evonik Degussa GmbH, Germany |
| Sylgard 309 | Product and trademark of Dow Corning, USA |

Synthesis

Preparation of $Me_3SiO[SiMeHO]_cSiMe_3$

An SiH-functional siloxane of the general formula $Me_3SiO[SiMeHO]_{1.2}SiMe_3$ was subjected to a fractional distillation under standard pressure. The fraction at a top temperature of 142° C. was determined with the aid of a gas chromatograph to be the product having a purity of 99% by weight of 1,1,1,3,5,5,5-heptamethyltrisiloxane. Thus, the product of the formula (V) has an index d of 1.01.

Subsequently, the distillate and the starting siloxane were mixed in such a way as to obtain the following siloxanes: $Me_3SiO[SiMeHO]_{1.2}SiMe_3$, $Me_3SiO[SiMeHO]_{1.15}SiMe_3$, $Me_3SiO[SiMeHO]_{1.10}SiMe_3$, $Me_3SiO[SiMeHO]_{1.05}SiMe_3$ and $Me_3SiO[SiMeHO]_{1.01}SiMe_3$.

The determination of purity was conducted with the aid of $^1H$ NMR and $^{29}Si$ spectroscopy. These methods, especially taking account of the multiplicity of the couplings, are familiar to those skilled in the art.

With the aid of these siloxanes, 21 samples were produced analogously to the general preparation method which follows.

General Synthesis Method for Hydrosilylation:

A 1000 ml three-neck flask equipped with stirrer and reflux condenser was initially charged with 0.5 mol of a polyether of the general formula $CH_2=CHCH_2O[CH_2CH_2O]_m[CH_2CH(CH_3)O]_nR^5$ and heated to 90° C. Subsequently, 10 ppm of Pt were added in the form of a toluenic solution of the Karstedt catalyst (Pt content 2 mol %). The mixture was stirred for 10 min and then 0.38 mol of SiH groups in the form of the SiH-functional siloxane $Me_3SiO[SiMeHO]_cSiMe_3$ was added dropwise within 15 min. An exothermic reaction was observed; the reaction mixture was stirred at 90° C. for a further 4 h. In all cases, it was no longer possible to detect any SiH functions by gas-volumetric means.

TABLE 1

Samples prepared; the $R^5$, c, m, n, M (PE) and m/n data relate to formula (I) and, respectively, to formula (II); in the cases when n = 0, m/n is undefined and consequently not stated:

| Sample | $R^5$ | c | m | n | M (PE) | m/n |
|---|---|---|---|---|---|---|
| Tego XP 11022 | H | 1.00 | 8.0 | 3.3 | 543 | 2.45 |
| Sample 1 | H | 1.01 | 7.8 | 0.0 | 343 | — |
| Sample 2 | H | 1.20 | 6.0 | 3.0 | 438 | 1.98 |
| Sample 3 | H | 1.01 | 10.0 | 0.0 | 440 | — |
| Sample 4 | Me | 1.01 | 7.8 | 0.0 | 343 | — |
| Sample 5 | H | 1.20 | 9.9 | 1.9 | 545 | 5.27 |
| Sample 6 | H | 1.01 | 14.6 | 0.0 | 642 | — |
| Sample 7 | Me | 1.01 | 12.3 | 0.0 | 541 | — |
| Sample 8 | H | 1.01 | 12.3 | 0.0 | 541 | — |
| Sample 9 | H | 1.01 | 9.9 | 1.9 | 546 | 5.27 |
| Sample 10 | H | 1.01 | 8.0 | 3.3 | 543 | 2.45 |
| Sample 11 | H | 1.01 | 6.2 | 4.7 | 545 | 1.32 |
| Sample 12 | H | 1.01 | 4.9 | 5.6 | 540 | 0.88 |
| Sample 13 | H | 1.01 | 3.4 | 10.2 | 741 | 0.33 |
| Sample 14' | H | 1.01 | 10.7 | 8.1 | 941 | 1.32 |
| Sample 15' | H | 1.01 | 14.4 | 7.0 | 1040 | 2.06 |
| Sample 16' | H | 1.05 | 8.0 | 3.3 | 543 | 2.45 |
| Sample 17' | H | 1.10 | 8.0 | 3.3 | 543 | 2.45 |
| Sample 18 | H | 1.15 | 8.0 | 3.3 | 543 | 2.45 |
| Sample 19 | H | 1.20 | 9.2 | 4.1 | 643 | 2.24 |
| Sample 20 | H | 1.20 | 3.4 | 10.2 | 741 | 0.33 |
| Sample 21 | H | 1.20 | 10.7 | 8.1 | 941 | 1.32 |

Samples 2, 5, 19, 20 and 21 are noninventive polyether siloxanes since the index c is too high. Samples 1, 3, 4, 6, 7 and 8 are noninventive since the index n is zero. Samples 5 and 9 are noninventive because the content of oxyethylene groups is too low.

Test Solutions:

0.1% by weight solutions of the test substances in distilled water were made up.

Spreading Test

Spreading was examined by applying a 50 μl droplet of the test solutions to a standard polypropylene film (of the Forco-OPPB type, from Van Leer). The droplet was applied with a micropipette. The area of spread was measured 90 seconds after the application. The experiments were conducted at 23° C. and a relative air humidity of 60%.

Surface Tensions

Surface tensions were measured by the Wilhelmy plate method with a Kruss K 12 tensiometer at 25° C.

OECD Biodegradability

Biodegradability was determined in accordance with OECD Method 301F by manometric respirometry at a temperature of 22° C.±1° C. The degradation rate was determined within 28 days. The samples had been analysed in a concentration of 100 mg/l and 28 mg/l both against a zero sample (mineral medium) and against a sodium benzoate solution of equal concentration. The values were recorded both after 14 days and after 28 days. After 14 days, no plateau phase had been reached yet. The sewage sludge samples used came from the sewage treatment plant belonging to the Ruhrverband water company, Sunthelle 6, 57392 Schmallenberg on 16 Sep. 2014. The concentration used was 29.6 mg of dry matter per litre of mineral medium; the pH was determined before the start of the experiments to be 7.4±0.2.

Results of the Interfacial Activity Study:

Comparative substances used for some commercial products, and substances according to U.S. Pat. No. 6,734,141.

Surfactant B: $Me_3SiO\text{-}[MeR'SiO]_{1.20}\text{—}OSiMe_3$, with $R'=\text{—}(CH_2)_3\text{—}O\text{—}(CH_2CH_2O\text{—})_{10}\ (CH_2CH(CH_3)O\text{—})_2\text{-}H$ Surfactant C: $Me_3SiO\text{-}[MeR'SiO]_{1.00}\text{—}OSiMe_3$, with $R'=\text{—}(CH_2)_3\text{—}O\text{—}(CH_2CH_2O\text{—})_{20}\ (CH_2CH(CH_3)O\text{—})_5\text{-}H$ Surfactant D: $Me_3SiO\text{-}[MeR'SiO]_{1.00}\text{—}OSiMe_3$, with $R'=\text{—}(CH_2)_3\text{—}O\text{—}(CH_2CH_2O\text{—})_{12.5}\text{-}H$ BREAK-THRU S 233: $Me_3SiO\text{-}[MeR'SiO]_{1.20}\text{—}OSiMe_3$, with $R'=\text{—}(CH_2)_3\text{—}O\text{—}(CH_2CH_2O\text{—})_{9.9}\ (CH_2CH(CH_3)O\text{—})_{1.9}\text{-}H$ BREAK-THRU S 240: $Me_3SiO\text{-}[MeR'SiO]_{1.20}\text{—}OSiMe_3$ with $R'=\text{—}(CH_2)_3\text{—}O\text{—}(CH_2CH_2O\text{—})_6\ (CH_2CH(CH_3)O\text{—})_3\text{-}H$ BREAK-THRU S 278: $Me_3SiO\text{-}[MeR'SiO]_{1.20}\text{—}OSiMe_3$ with $R'=\text{—}(CH_2)_3\text{—}O\text{—}(CH_2CH_2O\text{—})_{7.8}\text{-}Me$ SILWET L77: $Me_3SiO\text{-}[MeR'SiO]\text{—}OSiMe_3$ with $R'=\text{—}(CH_2)_3\text{—}O\text{—}(CH_2CH_2O\text{—})_8\text{-}Me$

| Adjuvant | Static surface tension [mN/m] | Spread diameter [mm] | Biodegradable |
|---|---|---|---|
| Tego XP 11022 | 22.9 | 70 | yes |
| Sample 1 | 21.6 | | no |
| Sample 2 | 21.7 | | no |
| Sample 3 | 21.6 | 53 | no |
| Sample 4 | 22.0 | 70 | no |
| Sample 5 | 21.4 | 15 | |
| Sample 6 | 22.8 | 15 | |
| Sample 7 | 22.7 | 15 | no |
| Sample 8 | 22.7 | 15 | yes |
| Sample 9 | 21.9 | 30 | |
| Sample 10 | 21.4 | 70 | yes |
| Sample 11 | 22.3 | 80 | |
| Sample 12 | 22.2 | 75 | |
| Sample 13 | | 16 | |
| Sample 14' | | 15 | |
| Sample 15' | 26.8 | 11 | |
| Sample 16' | 21.7 | 60 | yes |
| Sample 17' | 21.7 | 60 | yes |
| Sample 18 | 22.0 | 53 | yes |
| Sample 19 | 23.5 | 16 | |
| Sample 20 | 34.8 | 12 | |
| Sample 21 | 25.3 | 12 | |
| Surfactant B | 24.1 | 14 | |
| Surfactant C | 28.2 | 10 | |
| Surfactant D | 23.8 | 13 | |
| BREAK-THRU S 240 | 22.3 | 70 | |
| BREAK-THRU S 278 | 22.0 | 70 | |
| BREAK-THRU S 233 | 21.4 | 15 | |
| Silwet 806 | 23.5 | 70 | |
| Silwet L77 | 23.8 | 80 | |
| Silguard 309 | 23.0 | 80 | |

Typical superspreaders show a spread diameter in this test of 35 mm or more.

It is found that biodegradable superspreaders have a very defined structure.

The polyether has to have a certain molar mass, but must not be too heavy either. In addition, the polyether has to have a certain number of [CH$_2$CH(CH$_3$)O] groups, but a certain ratio between [CH$_2$CH(CH$_3$)O] and [CH$_2$CH$_2$O] groups still has to be maintained. Furthermore, the siloxane must not be too inhomogeneous.

The results show the advantageous use of the inventive substances.

Biodegradability Results:

| Adjuvant | Biodegradability [%] |
|---|---|
| Sample 8 | 60% |
| Sample 10 | 66% |
| Sample 1 | <60% |
| Sample 2 | <60% |
| Sample 7 | 7% |
| Sample 3 | <60% |

The results show the easy biodegradability of the inventive substances.

Greenhouse Experiments to Determine the Improvement in Biological Efficacy of a Herbicide In a greenhouse, common meadowgrass (*Poa pratense*) was grown in pots. As soon as the plants had reached a height of about 5 to 7 cm, they were sprayed with spray liquor that contained the herbicide Cato® (DuPont, Germany, active ingredient: rimsulfuron, concentration: 250 g of active ingredient/kg). The amount of spray that contained the active ingredient corresponded to 200 l/ha. Various adjuvants were added to the spray liquor. For each element of the experiment there were 3 pots that were treated in the same way. The pesticide dosage was 10 g/ha. Commercial standard wetting agents added to the tank were Break-Thru S240 and trisiloxane BREAK-THRU S233, each at 50 ml/ha. The dosage of Tego XP 11022 was 100 ml/ha. The damage to the plants by the herbicide treatment is compared here to untreated plants and the efficacy of the sprayed treatment is expressed as a ratio to the untreated plants. The efficacy was scored in each of the 3 pots per element of the experiment by methods known to those skilled in the art 14 and 28 days after the treatment. The average was calculated and reported as results in the table as a percentage compared to the control without herbicide treatment.

| Herbicide | Adjuvant | 14 d | 28 d |
|---|---|---|---|
| Cato, 10 ml/ha | none | 50% | 74% |
| Cato, 10 ml/ha | Tego XP 11022, 100 ml/ha | 70% | 94% |
| Cato, 10 ml/ha | BREAK-THRU S240, 50 g/ha | 60% | 84% |
| Cato, 10 ml/ha | BREAK-THRU S233, 50 g/ha | 50% | 83% |

The results show that the inventive composition brought a distinct increase in action compared to herbicide treatment without wetting agent. The advantageous use of the inventive compositions compared to the prior art is shown by this experiment.

The invention claimed is:

1. A composition comprising polyether-modified siloxanes of formula (I)

$$M_a D_b D'_c \quad \text{Formula (I)}$$

with M is R$^1_3$SiO$_{1/2}$, D is R$^1_2$SiO$_{2/2}$, D' is R$^1$R$^2$SiO$_{2/2}$, where a is 2
b is between 0 and 0.1,
c is between 1.0 and 1.15, R$^1$ are independently hydrocarbyl having 1 to 8 carbon atoms,
R$^2$ are independently a polyether radical of the formula (II)

—R$^3$O[CH$_2$CH$_2$O]$_m$[CH$_2$CH(CH$_3$)O]$_n$R$^5$   Formula (II)

where
m is from 3.4 to 11.0,
n is from 2.5 to 8.0,
and wherein m/n is from 1.9 to 2.8,
R$^3$ are independently divalent hydrocarbyl radicals having 2 to 8 carbon atoms,
R$^5$ is hydrogen
the polyether-modified siloxanes of formula (I) having a biodegradability of from 60% to 100% and wherein the molar mass of the polyether radical M(PE) is between 520 g/mol and 660 g/mol.

2. The composition according to claim 1, wherein the sum total of m+n is from 9 up to 19.

3. The composition according to claim 2, wherein a 0.1 percent by weight solution of the polyether-modified siloxanes of formula (I) in water has a spreading area of from 10 to 60 cm$^2$.

4. The composition according to claim 2, wherein the polyether-modified siloxanes of the formula (I) have an index c between 1 and 1.05, where the m/n ratio is 0.8 to 2.8 and a 0.1% by weight solution of these siloxanes in water has a spreading area of 15 to 60 cm$^2$.

5. The composition according to claim 1, wherein a 0.1 percent by weight solution of the polyether-modified siloxanes of formula (I) in water has a spreading area of from 10 to 60 cm$^2$.

6. The composition according to claim 1, wherein the polyether-modified siloxanes of the formula (I) have an index c between 1 and 1.05, where the m/n ratio is 0.8 to 2.8 and a 0.1% by weight solution of these siloxanes in water has a spreading area of 15 to 60 cm$^2$.

7. The composition according to claim 1, wherein the polyether-modified siloxanes of the formula (I) have a biodegradability of greater than 60%, and the index c is additionally between 1 and 1.05, where the R$^5$ radical is hydrogen and a 0.1% by weight solution in water has a spreading area of 15 to 60 cm$^2$.

8. An adjuvant in crop protection wherein the adjuvant comprises the composition according to claim 1.

9. A tank mix additive for spray liquors wherein the tank mix additive comprises the composition according to claim 1.

10. The composition according to claim 1, wherein the sum total of m+n is from 9.5 to 15.

11. The composition according to claim 1, wherein the sum total of m+n is from 10 to 12.

12. The composition according to claim 1, wherein b is 0, c is between 1.00 and 1.10, m is from 3.6 to 9.9, n is from 2.7 to 7.5, R$^3$ is selected from the group consisting of ethylene, propylene, 1-methylpropylene, 1,1-dimethylpropylene radical, and the polyether-modified siloxanes of formula (I) has a biodegradability of from 63% to 100%.

13. The composition according to claim 1, wherein b is 0, c is between 1.00 and 1.05, m is from 4.5 to 8.5, n is from 3.0 to 6.0, R$^3$ is —CH$_2$CH$_2$CH$_2$—, and the polyether-modified siloxanes of formula (I) having a biodegradability of from 65% to 100%.

14. The composition according to claim 1, wherein a 0.1 percent by weight solution of the polyether-modified siloxanes of formula (I) in water has a spreading area of from 15 to 50 cm$^2$.

15. The composition according to claim 1, wherein a 0.1 percent by weight solution of the polyether-modified siloxanes of formula (I) in water has a spreading area of from 20 to 40 cm$^2$.

16. A process for preparing polyether-modified siloxanes, comprising the steps of
a) purifying an H-siloxane of the formula (V)

$$M_a D_b D'_d \quad (V)$$

with $M=R^1{}_3SiO_{1/2}$, $D=R^1{}_2SiO_{2/2}$, $D'=R^1R^2SiO_{2/2}$, where
a is 2,
b is between 0 and 0.1,
d is between 1.16 and 3,
$R^1$ are independently hydrocarbyl having 1 to 8 carbon atoms,
$R^2$ is hydrogen
b) reacting the purified product of step a) in the manner of a hydrosilylation with a terminally unsaturated polyether of the formula (VI)

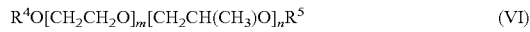

$$R^4O[CH_2CH_2O]_m[CH_2CH(CH_3)O]_nR^5 \quad (VI)$$

where
m is from 3.4 to 11.0, n is from 2.5 to 8.0,
wherein m/n is from 1.9 to 2.8,
$R^5$ are each independently hydrocarbyl radicals having 1 to 16 carbon atoms or hydrogen, preferably hydrogen or methyl, especially hydrogen,
$R^4$ are independently monovalent terminally unsaturated hydrocarbyl having 2 to 8 carbon atoms and
wherein the molar mass of the polyether radical M(PE) is between 520 g/mol and 660 g/mol.

17. The process according to claim 16, wherein the H-siloxane of the formula (V) is purified by employing a thermal separation process.

18. The process according to claim 16, wherein $R^1$ is selected from the group consisting of methyl, ethyl, propyl or phenyl radicals, m is from 4.5 to 8.5, n is from 2.7 to 7.5, wherein m/n is from 0.55 to 3.00,
$R^5$ is selected from the group consisting of hydrogen or methyl, and
$R^4$ is selected from the group consisting of $CH_2=CH_2-$, $CH_2=CHCH_2-$, $CH_2=CHCH(CH_3)-$, $CH_2=CHC(CH_3)_2$, especially preferably $CH_2=CHCH_2-$.

19. The process according to claim 16, wherein $R^1$ is a methyl radical, n is from 3.0 to 6.0, wherein m/n is from 0.8 to 2.8,
$R^5$ is hydrogen, and
$R^4$ is $CH_2=CHCH_2-$.

20. The process according to claim 16, wherein in m/n is from 1.9 to 2.8.

* * * * *